United States Patent [19]
Petelin et al.

[11] Patent Number: 5,436,542
[45] Date of Patent: Jul. 25, 1995

[54] TELESCOPIC CAMERA MOUNT WITH REMOTELY CONTROLLED POSITIONING

[75] Inventors: Joseph Petelin, Shawnee Mission, Kans.; William L. Chernoff, Chilliwack, Canada

[73] Assignee: Surgix, Inc., Shawnee Mission, Kans.

[21] Appl. No.: 188,029

[22] Filed: Jan. 28, 1994

[51] Int. Cl.$^6$ .............................................. G05B 19/37
[52] U.S. Cl. ................... 318/567; 318/568.1; 318/568.12; 128/777; 364/559
[58] Field of Search ................. 318/560–646; 128/777; 364/559; 250/216, 208.6; 356/139.03, 141.2, 152.1; 433/69, 27, 55

[56] References Cited

U.S. PATENT DOCUMENTS

| | | | |
|---|---|---|---|
| 4,355,645 | 10/1982 | Mitani et al. | 128/777 |
| 4,447,207 | 5/1984 | Kataoka et al. | 128/777 |
| 4,459,109 | 7/1984 | Radke | 433/69 |
| 4,595,022 | 6/1986 | Schorr | 128/777 |
| 4,649,504 | 3/1987 | Krouglicoff et al. | 364/559 |
| 4,765,345 | 8/1988 | Adib | 128/777 |
| 4,792,697 | 12/1988 | LeParquier et al. | 250/561 |
| 4,800,897 | 1/1989 | Nilsson | 128/782 |
| 4,836,778 | 6/1989 | Baumrind et al. | 433/69 |
| 4,838,696 | 6/1989 | Pryor | 356/375 |
| 4,956,794 | 9/1990 | Zeevi et al. | 364/559 |

OTHER PUBLICATIONS

*Robots Give a Helping Hand*, Medical Design & Engineering, Mar. 1992.
Ornstein, Mark, "*Laparobot*"—A Surgeon-Controlled Laparoscopic Manipulator, Aug. 2, 1994.
Armstrong Medical Robotics brochure, Aug. 2, 1994.

*Primary Examiner*—Paul Ip
*Attorney, Agent, or Firm*—Kokjer, Kircher, Bowman & Johnson

[57] ABSTRACT

A motorized mount for a laparoscopic camera, with the mount being remotely controlled based upon movements of the user's head. The camera mount is connected to the operating table and to the laparoscopic camera. Control means may cause motion of the mount to pan horizontally, tilt vertically, and zoom the camera. The control means receives input signals from a tracking device which determines the three-dimensional position of a special headset mounted on the user. A foot pedal is operatively connected to the control means. In a first setting of the foot pedal the user may move freely without causing camera movement. Upon moving the foot pedal to the second condition, the control means sets the position of the user's head as a null position. Thereafter, pivotal movement of the head to the left, right, up, or down, or translational movement of the head forward or rear, will result in similar movements of the camera. Only actual movement in a defined "positive" direction will cause movement, such as tilting the head upward from the null position. Movement back towards the null position is considered a "negative" direction, resulting in no camera movement. In this manner, the standard head movements to look in a particular direction will cause appropriate camera movements to simulate these movements with the camera.

17 Claims, 6 Drawing Sheets

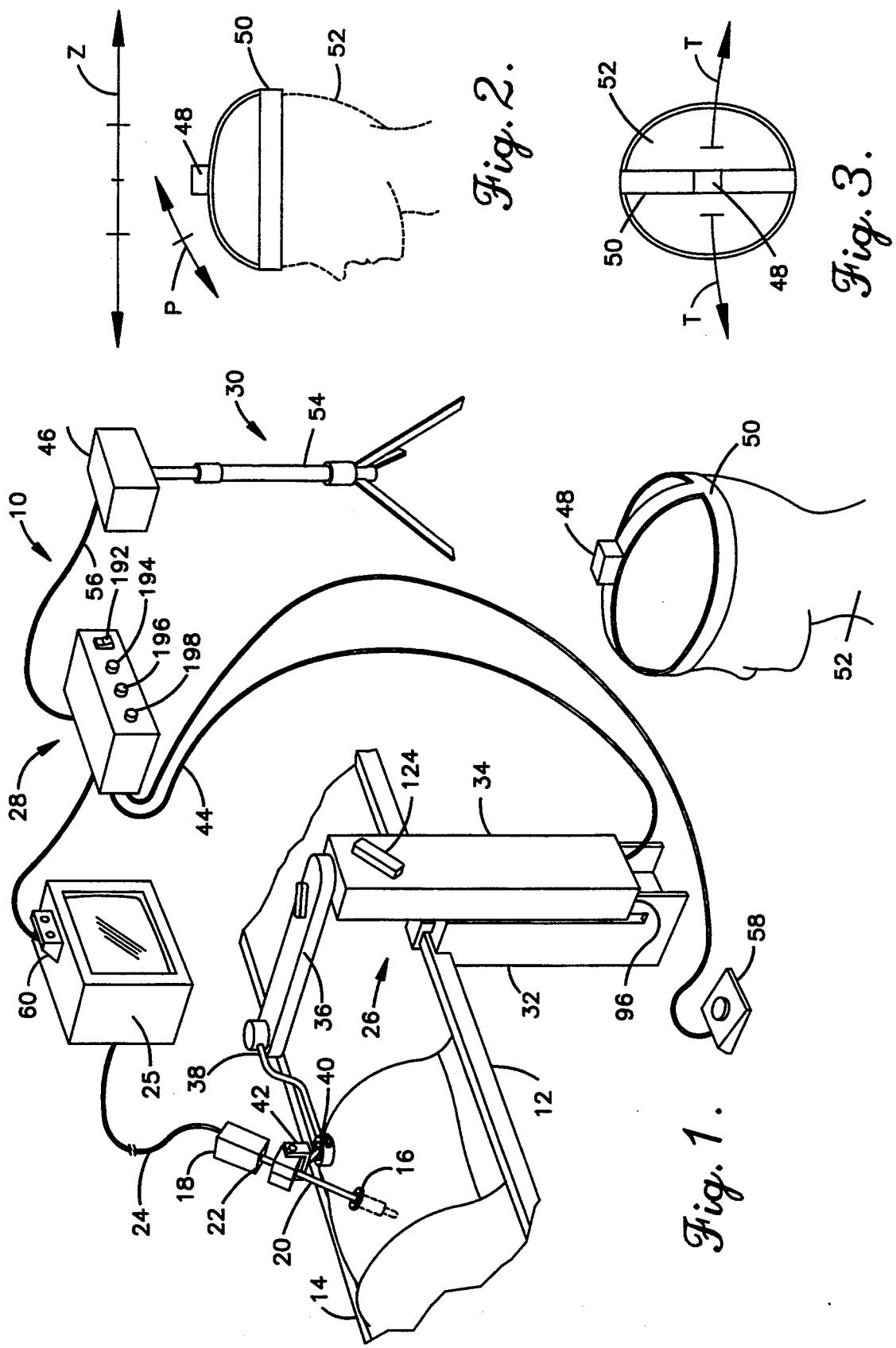

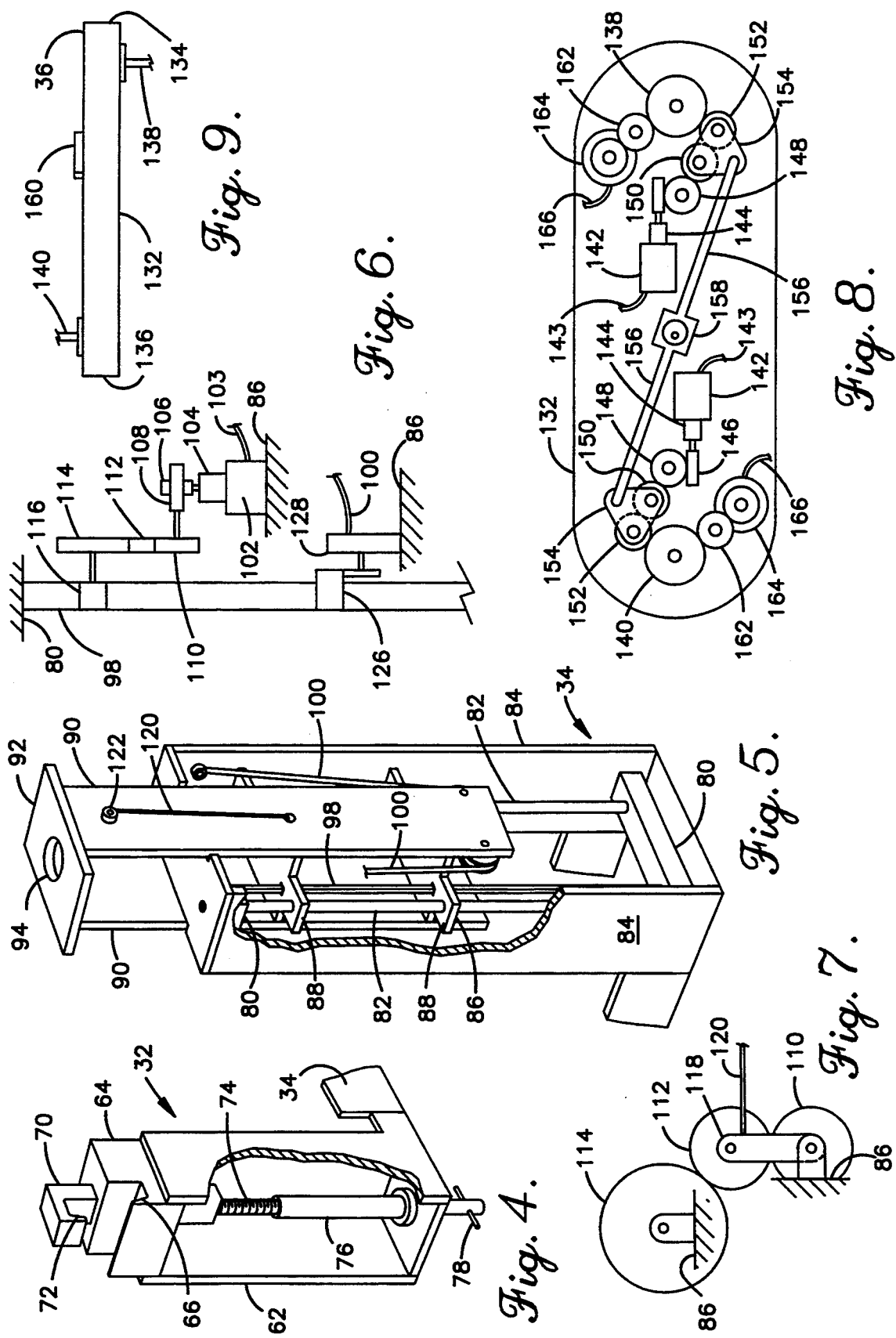

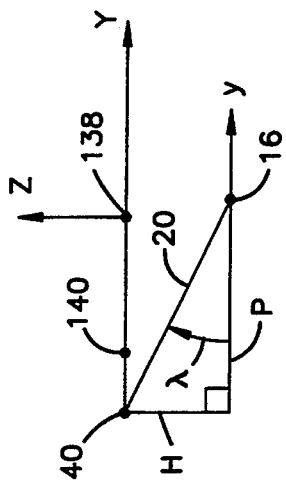
Fig. 11.
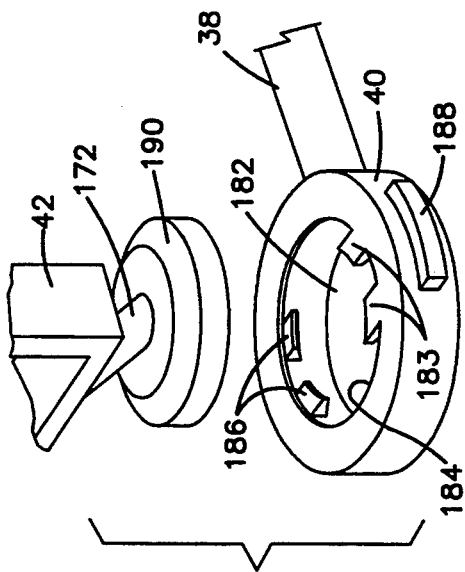
Fig. 13.
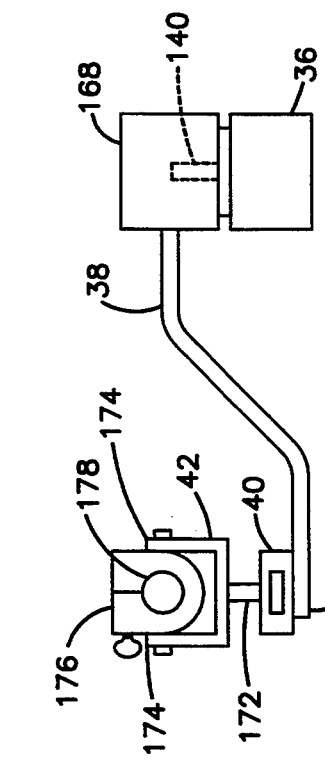
Fig. 10.
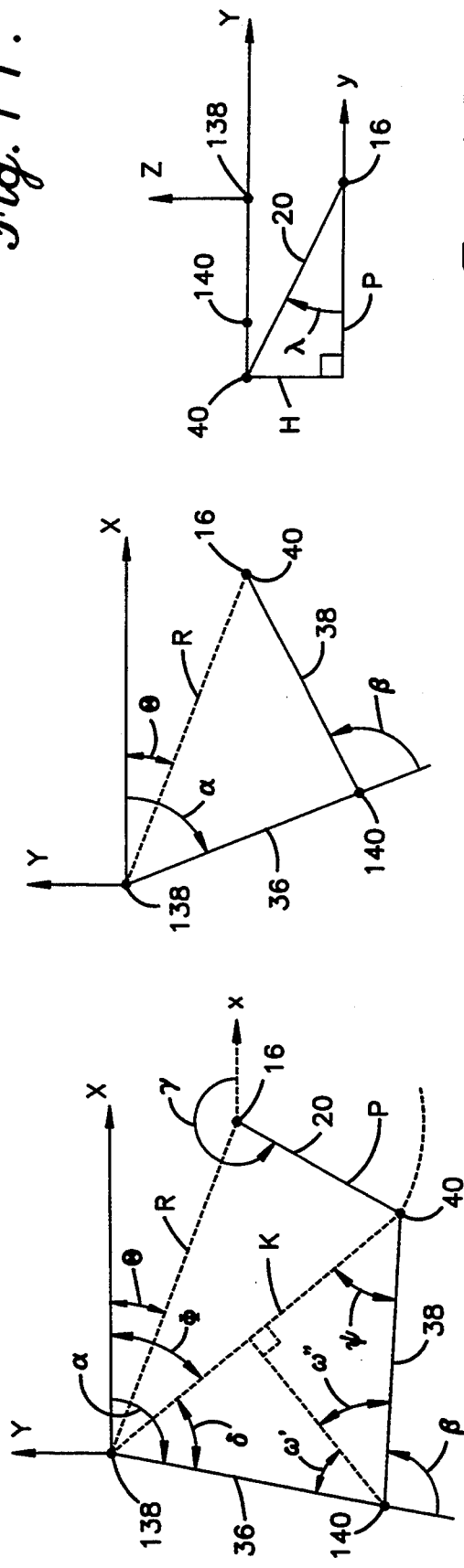
Fig. 12a.
Fig. 12.

TELESCOPIC CAMERA MOUNT WITH REMOTELY CONTROLLED POSITIONING

BACKGROUND OF THE INVENTION

1. Field of the Invention

The present invention relates in general to remote control of robotic-type apparatus, specifically telescopic cameras for surgery. In particular, the present invention relates to an improved mount for such cameras which will allow remotely controlled positioning of the camera.

2. Description of the Related Art

In recent years it has become increasingly popular to perform various medical procedures using telescopic techniques. In telescopic medical procedures, a plurality of trocars are connected to the patient, with each trocar extending through the body wall and forming a passage for various medical instruments. One of these medical instruments is the telescopic camera. These cameras are connected to a video monitor for real time imaging within the body cavity of the patient to assist the medical personnel in placement of the other medical instruments. Since the camera view must be varied during the procedure, this has typically required that one medical personnel be provided simply to control the laparoscopic camera position by manual holding and movement.

It has recently been proposed to support the camera by use of a motorized mount operatively connected to a foot-operated controller. The controller consists of a pad having several discrete buttons or switches. Depressing one of the buttons with the foot will result in a specific movement of the camera, and thus the view displayed upon the video monitor. This will allow the surgeon or other main medical personnel to directly control the position of the camera, and thus the video display.

SUMMARY OF THE INVENTION

An object of the present invention is to provide a robotic control system which will produce movements of an apparatus corresponding to movements of a portion of a body of the user, with the user being remotely positioned from the apparatus.

Another object of the present invention is to provide such a control system in which the motions of the user's head are tracked and used for control of the apparatus.

Yet another object of the present invention is to provide such a control system in which the apparatus is a motorized mount for a telescopic medical camera.

These and other objects are achieved by a motorized mount for a telescopic medical camera, with the mount being remotely controlled based upon movements of the user's head. The camera mount is connected to the operating table and to the camera. As is known, the camera is operatively connected to a video monitor to display a video image from the camera. The motorized mount is connected to a control means which may cause motion of the mount to pan horizontally, tilt vertically, and zoom the camera. The control means receives input signals from a tracking device. A tracking device determines the three-dimensional position of a special headset mounted on the user. A foot pedal is also operatively connected to the control means. In a first setting of the foot pedal, the motorized mount is inoperative, such that the user may move freely without causing camera movement. Upon activation of the switch to move the foot pedal to the second condition, the control means sets the position of the user's head as a null position. Thereafter, pivotal movement of the head to the left, right, up, or down, or translational movement of the head forward or rear, will result in similar movements of the camera. As such, the user may look directly at the video display at the moment the switch on the foot pedal is activated. Thereafter, if the user turns his or her head to the right, the camera view will pan to the right. Similarly, if the user lifts her or his head, the camera view will move upward. In this manner, the standard head movements to look in a particular direction will cause appropriate camera movements to effect these movements with the camera.

BRIEF DESCRIPTION OF THE DRAWINGS

The objects and features of the invention noted above are explained in more detail with reference to the drawings, in which like reference numerals denote like elements, and in which:

FIG. 1 is a detailed prospective view showing the present invention in use;

FIGS. 2 and 3 are explanatory views showing appropriate head movements according to the present invention;

FIG. 4 is a prospective view and partial cutaway showing an attachment portion for the mount according to the present invention;

FIG. 5 is a prospective view and partial cross-section showing a vertical positioning arm according to the present invention;

FIG. 6 is a schematic view showing the drive arrangement for the arm of FIG. 5;

FIG. 7 is a detailed schematic view of the gear arrangement of FIG. 6;

FIG. 8 is a schematic view showing the drive arrangement for a first pivot arm of the mount according to the present invention;

FIG. 9 is a side view of the first pivot arm of FIG. 8;

FIG. 10 is a side view of a second pivot arm according to the present invention;

FIG. 11 is a detailed prospective view showing a releasible mounting gimbal;

FIG. 12 is a schematic indicating the various angles of the pivot arms and camera;

FIG. 12a is a schematic indicating the various angles of the pivot arms during an initialization procedure;

FIG. 13 is a schematic indicating the angle and length of the camera;

FIG. 15 is a flowchart for an interrupt routine of the program of FIGS. 14 and 14a.

DETAILED DESCRIPTION OF THE INVENTION

Figure 14:
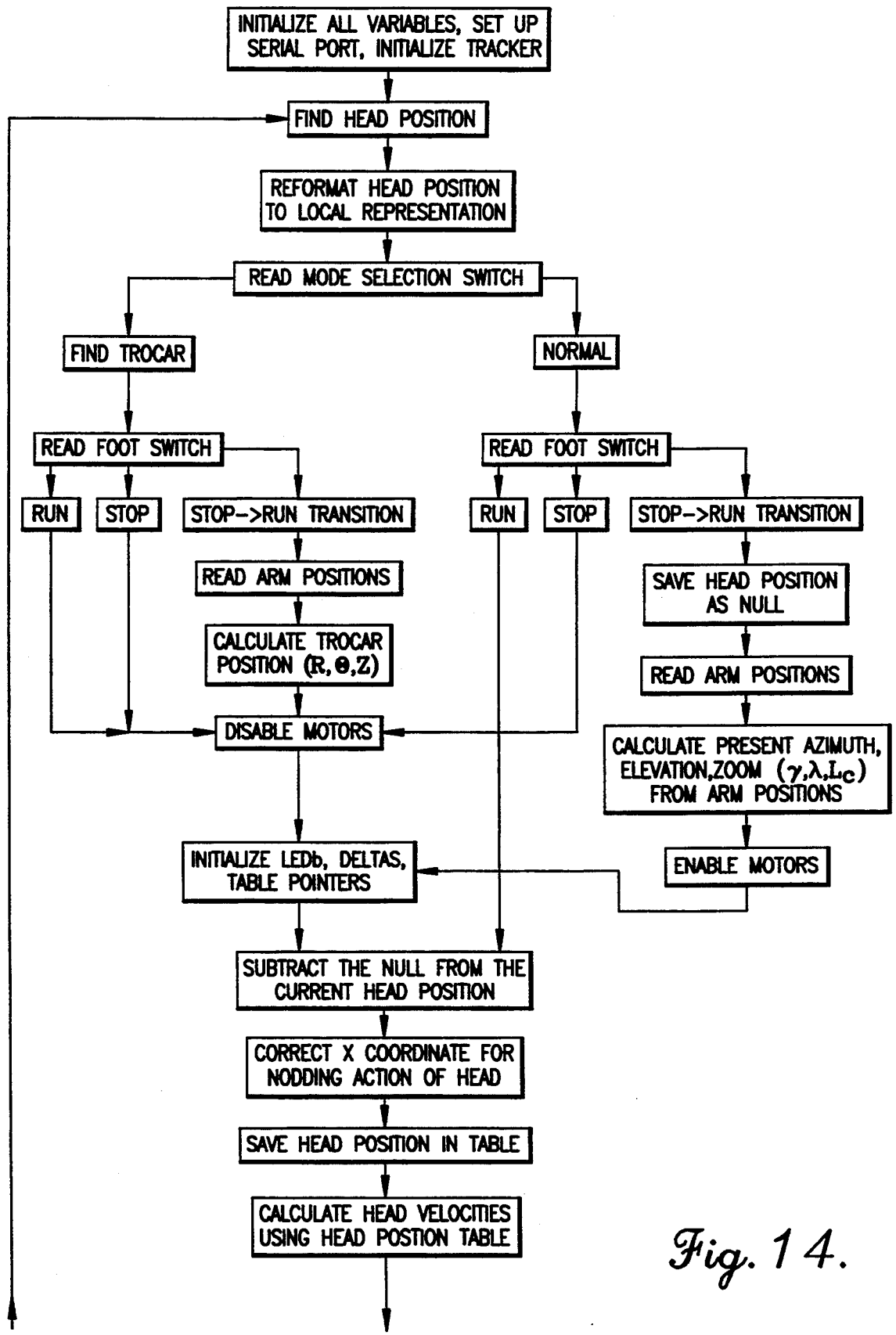
FIGS. 14 and 14a are flowcharts indicating program flow for the control means according to the present invention.
Figure 14A:
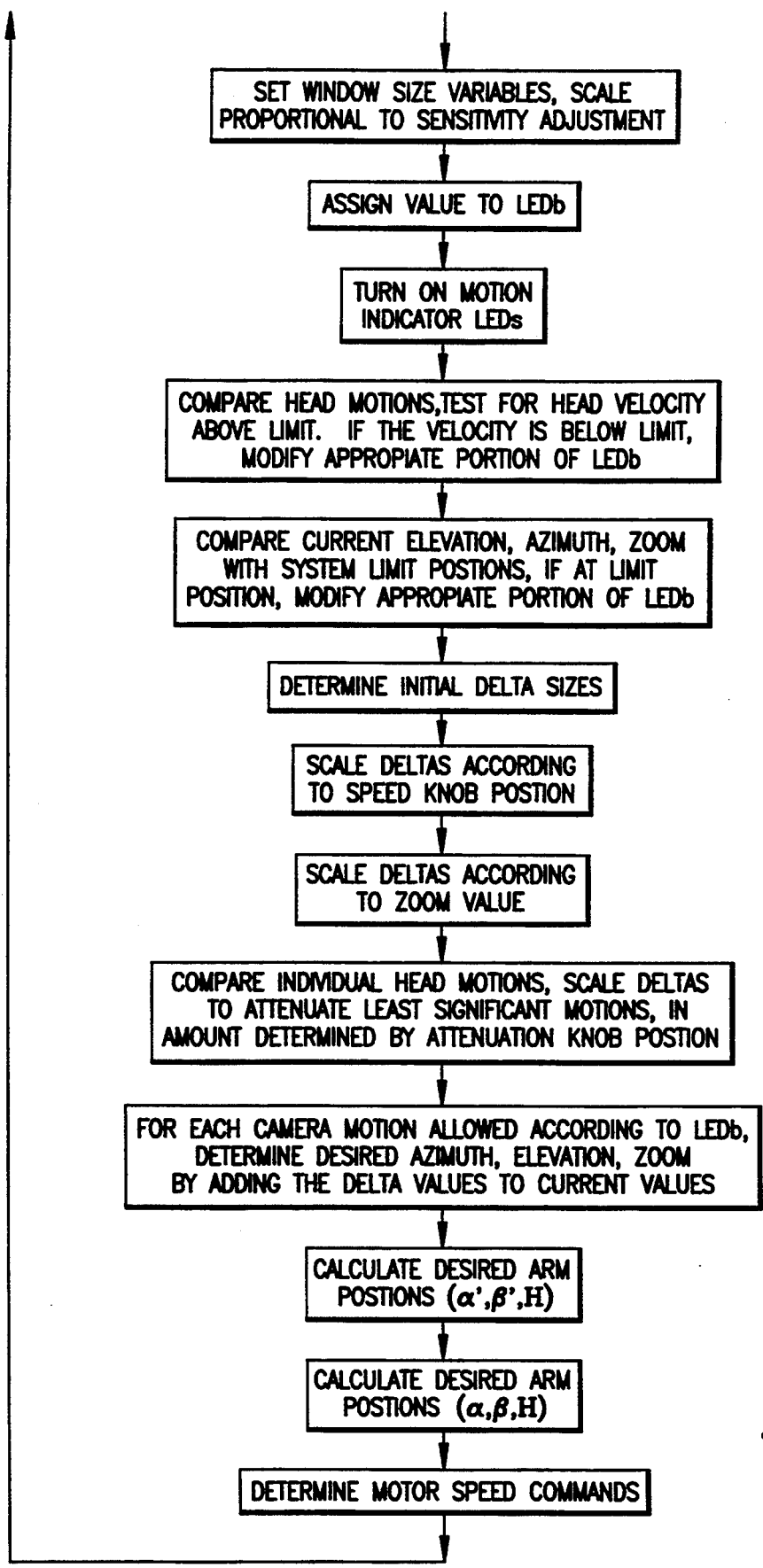

With reference to FIG. 1, a system according to the present invention is generally designated by reference numeral 10. The system according to the present invention may be employed in various applications, as noted more fully below. To aid in describing the system, however, one particular application for use in telescopic medical procedures referenced in detail. Additionally, within the general genus of telescopic medical procedures, the description of the system will be directed towards the specific use for laparoscopic medical procedures. It will be kept in mind, however, that the system is not so limited to use in laparoscopic applications.

The system 10 is shown employed with various prior art components. For example, there is shown a prior art operating or medical table 12. Upon this table 12 is a patient 14 which is typically, though not necessarily, human. The patient 14 has a prior art trocar 16 extending through the abdominal wall and providing access to the abdominal cavity. Although only a single trocar is shown, it will be understood that various other trocars may additionally be employed during any given procedure.

A prior art laparoscopic camera 18 includes an elongated shaft 20 having a circular cross-section with a camera lens and illumination means mounted at the free end. The camera 18 additionally includes various electronic circuitry within a housing 22 for producing a video signal which is transmitted, for example, upon line 24. The signals from the camera circuitry 22 are received by a prior art video display monitor 26. As such, the display monitor will show upon its screen an image corresponding to the view in front of the camera lens along the longitudinal axis of the shaft 20 of the camera.

As is known, the elastic nature of the abdominal wall allows the trocar 16 to be manipulated in various directions. In particular, the longitudinal axis of the passage extending through the trocar 16 will of course extend substantially normal to the abdominal wall at the location of the trocar 16 when in an unstressed, rest, position. As the camera shaft will closely pass through the passage in the trocar, the longitudinal axis of the camera shaft will initially correspond with the longitudinal axis of the trocar passage. However, if force is applied to the camera shaft, the trocar, and thus the camera shaft received therein, may be rotated about an infinite number of axes perpendicular to the original longitudinal axis of the trocar passage. This allows the camera to be positioned to view the desired location within the patient. Additionally, the camera shaft may slide with respect to the trocar during use to provide a zoom feature.

The system 10 according to the present invention is employed with these prior art elements to allow the camera to be positioned via remote control.

The system 10 generally includes a camera mount 26, a control means 28. The control means 28 includes an input 30 and will receive input signals from the input 30 and position signals from the mount 26, and in response will produce control signals directed to the mount 26. These control signals will cause the mount 26 to move in a predetermined manner, thus causing movement of the camera 18 to reorient the view displayed upon the monitor 25.

The camera mount 26 generally includes a table attachment section 32 which will secure the mount to the table 12. Connected to the table attachment section 32 is a lift arm 34. The lift arm 34 is mounted for movement, and specifically translation, in the vertical direction. The lift arm 34 in turn mounts a first pivot arm 36. The first pivot arm 36 may rotate about a vertical axis at its connection with lift arm 34.

At a position spaced from the lift arm 34, the first pivot arm 36 in turn mounts a second pivot arm 38. The second pivot arm also rotates about a substantially vertical axis, and at a position spaced from this axis there is mounted a gimbal pivot 40. The gimbal pivot 40 may rotate freely with respect to the second pivot arm 38 about a substantially vertical axis. The gimbal pivot 40 releasably mounts a camera gimbal 42. The gimbal 42 attaches to the camera shaft 20 in a manner which prevents translation of the shaft 20 along its longitudinal axis with respect to the gimbal, yet which allows pivotal movement of the shaft about a horizontal axis.

As may be envisioned, the mount 26 according to the present invention is capable of moving the camera 18 to a large number of positions. For example, from any given position, the lift arm 34 may be raised or lowered, and the pivot arms rotated, allowing the gimbal to move in a vertical arc about the trocar. This will cause the camera shaft to pivot about a horizontal axis due to the camera gimbal 42, thus moving the camera view upward or downward. Additionally, the first and second pivot arms 36 and 38 may be rotated such that the gimbal pivot 40 moves in a horizontal arc about the trocar 16. As the gimbal pivot 40 is freely rotatable with respect to the second pivot arm, this will cause the camera shaft to be pivoted left to right, causing a corresponding left to right pan in the view displayed by the monitor 25. Finally, the lift and pivot arms may be moved such that the gimbal pivot 40 translates in a radial direction with respect to the trocar 16. This will cause the camera shaft 20 to slide inward and outward with respect to the trocar, thus providing a zoom feature.

Various motor means are employed to cause the vertical translation of the lift arm 34, the pivoting of the first pivot arm 36 with respect to the lift arm, and the pivoting of the second pivot arm with respect to the first pivot arm. These motor means are operatively connected to the control means 28, as by a line 44. The control means 28 will consist of various microprocessor and memory means, typically with various adjustment knobs and switches provided. The control means provides control signals to the mount 26 to affect the various motor means to thus cause the desired motion of the mount to achieve the desired camera position. These control signals are determined based upon input signals from the input 30 and position signals from the mount 26.

The input 30 may be any device for remotely sensing at least one position and/or orientation of a portion of the human body, either with respect to another portion of the body, or with respect to the ground. The input preferably consists of a non-contact, three-dimensional position and orientation sensor, which generally includes a sensed unit 46 and a sensing module 48. The sensing unit 46 preferably has no physical connection with the module 48, yet the input 30 will produce signals indicating the three-dimensional position and orientation of the module 48. Various suitable devices are commercially available, for example an acceptable input is available from Ascension Technology Corp. of Burlington, Vt. under the designation The Flock of Birds ™ stand-alone model.

As is shown in FIG. 1, the module 48 is mounted upon a headset 50 worn by a medical personnel 52, such that the module 48 is located generally centrally at the top of the head. Since the module 48 will therefore be several feet above the ground during use, it may be preferable to provide the sensing unit 46 with a support 54 such that the sensing unit is at approximately the same vertical position as the module 48. As noted above, the input 30 will determine the position of the module 48, and will thus generate input signals used in the control means 28, with these signals typically being transferred via lines 56.

As the module 48 is mounted upon the headset 50, and the input 30 tracks the position of the module to provide the input signals, it should be apparent that it is the motion of the head which is used to control the motion of the mount 26 in this embodiment, and thus the camera position. Since the input provides signals used in the control means, with the control means using these signals to produce an output which controls the mount, any particular head position or motion may be assigned to correspond with any resultant mount movement or camera position.

With the commercial input means described above, it is possible to track the three-dimensional position and orientation (six degrees of freedom), and as such all possible head positions or motions are available. While any one of these possibilities may be employed, it is preferred that the system of the present invention operate in an intuitive manner, and as a natural extension of the user. This reduces training time with the system, reduces operator frustration during use, and reduces the possibility of undesired camera movement.

In normal life, if it is desired to look at something to the left, it is a natural reaction to turn the head to the left by pivoting about the neck. Similarly, when it is desired to look at something above the current field of view, it is natural to tilt the head upward about the neck. When it is desired to look at something closely, it is natural to move the head forward to bring the eyes closer to the object. Opposite movements are believed natural for opposite responses. Since these particular movements are natural and comfortable, these are the preferred head movements to cause associated movement of the camera position in the present system.

In particular, with reference to FIG. 2, an arrow P indicates the approximate movement of the module 48 if the user moves his or her head up or down in a nodding motion. This nodding motion will, of course, result in a slight rotation of the module 48 about a horizontal axis extending laterally of the user, in addition to a translation of the module. Similarly, the arrow Z shows the approximate movement of the module 48 if the user moves the head forward or rearward, such as by physically taking a step forward or backward, or leaning inward or rearward. Finally, with reference to FIG. 3, the arrows T indicate the movement of the module 48 if the user turns his or her head to the right or left. As above with the nodding motion, in addition to translation, this will also result in a small rotation of the module about a vertical axis. As may be seen, these various movements of the module caused by the motion of the user's head are readily discernible by sensing the translation, rotation, and/or both of the module.

It is possible for the camera position to track directly upon all movement of the module 48. For example, if the user looked to the left and upward the camera would pan to the left and pivot the lens upward. The user would then maintain his or her head in this position until a new camera angle was desired, at which point the user would move his or her head to that new position. While such an arrangement may be suitable in certain applications, in the present application of telescopic procedures, it is believed that this could result in undue neck and eye strain upon the user.

As such, it is preferred to define a center or null point, represented by the mark at the center of each of the lines P, Z, and T, with the possible motions emanating outward. Movement of the user's head in any of the directions, for example to the left, will cause a resultant camera movement, in this case a pan to the left. However, from this point the movement of the user's head back toward the null position does not register as a movement until the user again passes beyond the null position in that direction. This will result in the camera position being maintained, even though the user has brought his or her head back to a more comfortable, centered position.

In other words, each of the six possible user motions (three general motions, each in two direction) emanate outward from the null position, are positive in this outward direction, but are negative in the inward direction. It is only those motions in the positive direction which are converted into camera movement in this embodiment. Therefore, movement of the body, and thus the module, beyond the null position into one of the possible directions will result in movement of the camera so long as the motion of the module is in the positive (outward) direction only. A halt in movement, or movement of the module in the negative (inward) direction will not result in movement.

Put yet another way, it may be useful to consider this as a ratchet and pawl effect. Imagine that the user rotates his or her head 15 degrees to the right. Initially, the module will move beyond the null point into a right-hand movement area, with 15 degrees of head movement coming thereafter. This 15 degrees of outward head movement is translated into a corresponding camera pan to the right. As such, a "ratchet" is engaged with a "pawl" when there is outward movement away from the null point. Now imagine that from this 15 degree position the user moves his or her head ten degrees back towards the null position. This is an inward, negative, movement towards the null position, and as such the "ratchet" will slide over the "pawls" and there will be no corresponding camera movement. From this point, movement of the user's head back to the right ten degrees (15 degrees to the right of null) will result in a corresponding camera movement, as the "pawls" are engaged. As such, a repetitive back-and-forth movement within any of the directions will result in multiple discrete movements in that same direction.

Various other arrangements for causing movement are of course available. For example, in each of the directions of movement, there may be defined a certain null area (represented by the marks symmetric about the center of each of the lines P, T, and Z and FIGS. 2 and 3, although an angular null area may be used) where no camera movement will result from a head movement. Only when the user moves his or her head a sufficient extent to pass beyond this null area will movement occur. This transition between the null area to the movement area may be used as an on-off switch, such that so long as the user's head remains beyond the null area movement will continue, regardless of head movement of the user. (This is in contrast to the preferred control method, where camera movement results from head movement, and holding the user's head still, even beyond the null position, will not result in movement.)

Of course it is possible to combine aspects of this null zone arrangement with the preferred method described above. Specifically, a small amount of head movement in any of the directions will be tolerated and will not result in any movement, simply as a way to avoid unwanted camera movements due to spurious head movements. Beyond this null area, the standard rules apply as described above, with outward, positive, movement resulting in camera movement while inward, negative, movement, or a lack of movement, does not.

As may be envisioned, during many applications, and especially during medical procedures, the user will be moving about the room and turning his or her head to view various pieces of equipment. Each of these movements would be interpreted by the control means as an input and be used to control the camera position. To prevent this from happening, the control means 28 is preferably provided with a control switch 58. The control switch 58 preferably takes the form of a foot switch such that the user's hands are left free. Various other switch arrangements, such as voice activated, may of course be employed.

With the control switch 58, the user may place the control means 28 in either a run condition or a stop condition. Specifically, in the run position the input signals provided by the input 30 will be used by the control means to cause movement of the camera mount and thus the camera. However, in the stop condition the control means 28 will not provide output signals (or these signals will not be used), such that the user may freely turn his or her head and move about the room without causing camera movement.

As a further preferred arrangement, and as is better described below, the control means will preferably take the position of the module 48 at the moment of transition between the stop to the run condition as the null position described above. In practice, it would be very difficult to define some permanent null position in space which the user must return to each time, especially after the control means has been in the stop condition and the user has moved about the room. By defining the null position each time the control means moves from the stop to the run condition, it is assured that the user is well familiar with the null position and may more accurately control the camera movement.

As a further safeguard, the control means 28 also preferably includes an indicator 60. The indicator 60 will consist of at least one light (preferably in the form of an LED) which will provide an indication of the stop or run condition of the control means. In the preferred embodiment, the indicator 60 will be provided with a green LED and a red LED, with these LEDs being individually illuminated in the run and stop conditions, respectively. This will provide the user with a ready indication of the condition of the control means, such that unwanted camera movements due to unintentional head movements may be reduced. For ease of use, it is preferred that the indicator 60 may be readily mounted on the monitor 25 such that it may be easily viewed by the user, who typically faces this monitor.

With the general layout and operation of the system having thus been described, attention will now be directed to the particular construction of the system 10 according to the preferred embodiment.

With reference to FIG. 4, there is shown the table attachment section 32. The attachment section 32 generally consists of a vertically elongated attachment frame 62, having at its upper end a clasp block 64. The clasp block 64 includes a laterally extending bight portion 66 adapted to abut against a portion of an edge of the table 12.

The clasp block 64 additionally includes a vertically oriented passage 68 extending therethrough. Mounted within the passage 68 is a pinch block 70 adapted for sliding within the passage. The pinch block 70 includes a clasp portion 72 in close proximity to the bight 66, such that the clasp portion together with the bight 66 may compressively engage a portion of the table 12.

To provide the compressive force necessary to maintain the attachment section 32 in position on the table, the lower end of the pinch block 70, preferably extending below the clasp block 64, is provided with a threaded shaft 74 fixed thereto. The shaft 74 is vertically oriented, and is engaged by a internally threaded adjustment rod 76. The adjustment rod 76 is mounted for rotation, but not translation, at the lower end of the attachment frame 62, with the lower end of the adjustment rod 76 extending below the frame 62. This lower end is provided with an appropriate manual handle 78 such that the adjustment rod may be rotated with respect to the frame.

This rotation will cause the threaded shaft 74 to be drawn into, or moved out of, the adjustment rod 76. As the shaft 74 is fixed with respect to the shaft 74, the pinch block 70 will move upward and downward upon rotation of the adjustment rod. In this manner, the edge of the table may be securely clamped by the attachment section 32.

Adjacent its lower end, the attachment section 32 is rigidly secured to the lift arm 34. As is best shown in FIG. 5, the lift arm 34 includes a pair of vertically spaced support blocks 80 which serve to mount a pair of vertically extending slide rods 82. While the slide rods 82 may be sufficient to support the remaining structure to be described, it may be preferred to provide a pair of side panels 84 extending between the vertically spaced support blocks 80 and secured thereto.

A support carriage 86 is mounted upon the slide rods 82 for vertical movement along the slide rods. The carriage 86 may take various forms, but preferably has the form of two vertically spaced, horizontally extending carriage panels 88. As each of the carriage panels 88 may freely slide upon the rods 82, the panels 88 are maintained in their spaced configuration by rigid connection with a pair of vertically extending lift panels 90. The lift panels 90 have, at their upper end, a pivot plate 92 secured thereto and therebetween. The pivot plate 92 is located vertically above the upper support block 80 such that the lift panels 90 and pivot plate 92 may move with the carriage 86 in the vertical direction. As will be described more fully below, the pivot plate 92 includes an arm attachment opening 94 which will be used to connect the first pivot arm to the pivot plate 92.

Although not apparent in FIG. 5, it may be desirable to size the pivot plate 92 such that it extends peripherally outward beyond the side panels 84. A plurality of cover panels 96 (FIG. 1) may then be secured about the periphery of the plate 92 to extend over the support blocks, slide rods, etc. within the lift arm. This will improve the aesthetic appearance of the system, reduce contamination of the slide rods and carriage, and reduce the possibility of grease or other materials from the system 10 contaminating the outside environment.

The lift arm 34 will be provided with means for moving the first pivot arm in the vertical direction, and in particular the carriage 86 will be provided with a means for moving the carriage with respect to the slide rods. This means may take many forms, but preferably includes a rack 98 secured between the support blocks 80 and extending in proximity to, or preferably through, the carriage panels 88. Further portions of this means are discussed below.

As the carriage, lift panels, pivot plate, and pivot arms of the system will have an appreciable weight, it is preferred that the lift arm 34 be biased to compensate for this weight for reasons described more fully below. One method for biasing is to provide one or more springs 100, preferably constant force springs, mounted upon reels rotatably connected to the lower end of the lift panels 90. The free ends of the springs may be connected to the side panels 84, such that the carriage is biased upward against the weight of the remainder of the system.

With reference to FIG. 6, there is shown one example of a motor means included in the means for providing vertical movement of the carriage with respect to the slide rods. As may be seen, the rack 98 will extend vertically, and will have appropriate teeth upon an outer edge. An electric motor 102 is secured to the carriage, and is operatively connected to the control means, for example via line 103. The output shaft of the motor is connected via a slip clutch 104 to a driving gear 106. The driving gear 106 will be in meshing engagement with a first lift gear 108, with this lift gear 108 positively driving a pivot gear 110. The pivot gear 110 will drive a travel gear 112, which may in turn mesh with a second lift gear 114. This second lift gear 114 will be connected via a shaft to a lift pinion 116 engaged with the rack 98. Each of these gears is connected, at least in a general sense, to the carriage.

As may be envisioned, activation of the motor 102 will cause the various gears to rotate, thus causing the carriage, to which the motor and gears are secured, to move vertically upward or downward due to the engagement with the rack. While simpler gear arrangements are certainly possible, this particular arrangement is preferred as it allows the motor 102 to be selectively disengaged from the lift pinion 116.

In particular, with reference to FIG. 7 it may be seen that the pivot gear 110 is secured to the carriage 86 for rotation. The shaft of pivot gear 110 mounts a pivot lever 118, with the travel gear 112 being mounted upon the lever 118, rather than to the carriage 86. As may be envisioned, rotation of the pivot lever 118 will cause the travel gear 112 to engage or disengage from the second lift gear 114, while remaining in engagement with the pivot gear. This will in turn allow the motor 102 to be engaged or disengaged from the pinion 116.

To allow for selective engagement and disengagement, the pivot lever 118 connected to a manual actuator on the exterior of the mount. This may take the form of a release line 120 extending away from the carriage such that it may be manually pulled and released to cause the engagement and disengagement of the travel gear 112. One effective means for allowing this manual pulling is to cause the release line 120 to be run along the exterior of the outer lift panel 90, and be secured to the outer periphery of a crank 122 which is rotatable upon the lift panel (FIG. 5).

As is best shown in FIG. 1, a lift release handle 124 is provided on the exterior of the lift arm 34, and in particular on the exterior of the cover panel 96. The release handle 124 will have an end which extends through the panel 96 and is secured to the crank 122. In this manner, manual rotation of the handle 124 will result in rotation of the crank 122, thus causing the line 120 to be drawn about the periphery of the crank. This in turn draws the line away from the carriage, thus releasing the motor from engagement with the pinion. This will allow lift arm 34 (and the pivot arms connected thereto) to be raised and lowered manually without the need to overcome the friction provided by the motor. Appropriate spring biasing will of course be provided to bias the travel gear into meshing engagement.

For the control means 28 to provide accurate movement, the control means must of course know the various positions of the elements of the system. As such, the system 10 must have a sensor to note the vertical position of the carriage with respect to the slide arms. To effect this, there is provided a sensor gear 126 in engagement with the rack 98, with the sensor gear 126 being connected to a rotary sensor 128. The sensor 128 is operatively connected to the control means 28, for example by means of a line 130.

The sensor 128 may be of any conventional type, such as a rotary potentiometer, or an optical rotary sensor. Alternatively, the vertical position of the carriage with respect to the slide rods may be determined by a linear position sensor extending parallel to the slide rods, or by other sensors.

It is noted that the rotary sensor 128 is connected to the rack via its own sensor gear 126, rather than the gearing employed for the motor 102. A portion of the gearing for the motor 102 may be employed to drive the sensor 128, however care must be taken that the drive for the sensor is taken at a position which will not be disengaged upon activation of the lift release lever 124. This is necessary to allow the sensor 128 to track the vertical movements of the slide arm even if these vertical movements are manual, rather than as a result of the activation of motor 102.

As noted above, the first pivot arm 36 is mounted to the lift arm 34, and in particular to the pivot plate 92. The first pivot arm 36 is best shown with reference to FIGS. 8 and 9.

As is shown in FIG. 9, the first pivot arm 36 includes an elongated outer housing 132 having first and second ends 134 and 136. Extending outward from the first end 134 is a first drive-shaft 138. The first pivot arm will include means for rotating the first pivot arm with respect to the slide arm, and in particular appropriate motor means to drive the shaft 138 with respect to the first pivot arm. As such, securing the drive shaft 138 to the plate 92 of the lift arm, via a nut for example, will permit rotation of the first pivot arm with respect to the lift arm 34. An appropriate bearing will of course be inserted between the plate 92 and the lift arm 34 to ease this pivotal movement.

In a similar manner, there is provided means for rotating the second pivot arm with respect to the first pivot arm. In particular, this means will include the second end 136 of the first pivot arm having a second drive shaft 140 extending outwardly therefrom in a parallel, offset relation from the first shaft 138, and motor means to rotate this shaft 140 with respect to the first pivot arm. Although not strictly required, it is preferred that the first shaft 138 extend vertically downward, while the second shaft 140 extends vertically upward.

The second shaft 140 will be connected in a rigid manner to the second pivot arm 38 to allow the second pivot arm to rotate with respect to the first pivot arm. While the motor means to cause the rotation of the second pivot arm with respect to the first pivot arm may be alternatively be mounted within the second pivot arm 38, it is preferred that this motor means be mounted within the first pivot arm 36, along with the motor means for causing the first pivot arm to rotate with respect to the lift arm. This is to allow the weight of the motor means to be closer to the lift arm, and thus reduce the moment applied to the pivot arms and lift arm.

With reference to FIG. 8, there is shown a top view of the first pivot arm 36, with the upper face of the housing 132 removed to show the motor means for rotating the shafts 138 and 140. The majority of these motor means are identical for both shafts, and as such similar reference numerals will be employed.

For each of the shafts 138 and 140 there is provided a motor 142, operatively connected to the control means 28, for example by lines 143. As with the lift arm, each motor 142 is connected via a slip clutch 144 to a driving gear 146. The driving gears 146 are each in turn engaged with a first arm gear 148, which is in turn engaged with a pivot gear 150. The pivot gear 150 is in turn engaged with a travel gear 152, which is engaged with a plurality of teeth upon the exterior of the shaft 138 and 140. As such, rotation of the motor 152 will be transmitted via the slip clutch and various gears to the shafts 138 and 140.

As with the lift arm, it is preferred that the motor means for pivoting of the arms also be capable of disengagement. As such, in a manner similar with the lift arm, each of the pivot gears 150 is secured for rotation to the arm 36, and mounts upon its axis of rotation a pivot lever 154. The travel gears 152 are mounted for rotation upon the associated pivot levers 154, rather than to the first pivot arm 36 directly. As such, rotation of the pivot lever 154 will cause engagement and disengagement of the travel gear 152 with the associated drive shaft 138 or 140, while the travel gear remains engaged with the associated pivot gear.

To effect the pivoting of the levers 154, and thus disengagement of the drive shafts, each of the pivot levers 154 is connected to a first end of an activation rod 156. The elongated activation rods extend toward the center of the first pivot arm 36 with the second ends of the activation rods each having a circular passage therethrough. An eccentric cam member 158 is pivoted at its lower end to the housing 132 to define an axis of rotation. A pair of cams, one for each activation rod, are offset about this axis of rotation and are received within the associated openings of the rods 156.

As such, rotation of the cam member 158 will cause the associated ends of the rods 156 to be drawn inward due to camming action, thus causing the pivot levers 154 to rotate in the clockwise direction (as shown in FIG. 8) to disengage the travel gears from the associated drive shafts. To allow simple manual rotation of the cam member 158, and thus disengagement of the motor means, the upper end of the member 158 passes through the upper face of the housing 132 and is secured to an arm release handle 160 FIG. 9). As such, manual rotation of the arm release handle 160 will permit engagement or disengagement of the motor means with each of the shafts 138 and 140. This will allow the pivot arms to rotate freely with respect to the lift arm.

As noted before with regard to the lift arm, the control means 28 must be constantly informed of the relative positions of the various arms. As such, each of the shafts 138 and 140, at their toothed periphery within the housing 132, is connected to a sensor gear 162, which is in turn engaged with a rotary position sensor 164. The sensors 164 are operatively connected to the control means 28, for example by lines 166. As with the lift arm, it is noted that the sensors 164 are directly connected to the shafts 138 and 140, respectively, such that engagement and disengagement of the motor means with these shafts will not have any effect upon the position sensor. This allows the control means 28 to have accurate information as to the position of the arms even if the motors are disengaged. For further precision, the sensors may be directly connected to the associated shafts, thus eliminating the backlash errors associated with intermediate gears.

With reference to FIG. 10, the second pivot arm 38 is shown mounted upon the first pivot arm 36. In this figure, the first pivot arm is viewed along its longitudinal axis, with the drive shaft 140 extending upwardly therefrom. The second pivot arm 38 is rigidly secured to the drive shaft 140, preferably with a bearing located between the pivot arms to ease relative rotation. The second pivot arm 38 is essentially a rigid elongated member, although it preferably has a downward "S" curve as shown in FIG. 10. This downward curvature of the second pivot arm allows the end of the camera gripped on the pivot arm to move further downward without the first pivot arm abutting against the patient, which in turn allow the view provided by the camera to be elevated to a grater extent.

The second pivot arm is connected to the first pivot arm at a first end 168, and has a second end 170 extending outwardly from the first pivot arm. It is at the second end 170 that the camera 18 is mounted.

In particular, the second end 170 of the arm 38 rotatably mounts the gimbal pivot 40. Pivot 40 is mounted for rotational movement about a vertical axis with respect to the arm 38. Mounted to this gimbal pivot 40 is the camera gimbal 42.

The gimbal 42 includes a rigid support 172. As best shown in FIG. 1, while the support may be vertical, it is preferred that it be angled outward, for reasons described below. Connected to the support 172 are a pair of spaced arms 174 forming a general "U" configuration. Mounted between the arms 174 is a camera shaft lock 176, which includes a camera shaft opening 178 extending therethrough. The shaft opening 178 is slightly larger than the camera shaft diameter, such that the camera shaft 20 may freely slide therethrough.

The shaft lock 176 additionally includes a groove extending from its exterior to the shaft opening 178. A thumb screw 180 extends freely through a passage which is normal to this groove, and extends from the exterior of the lock to the groove. The threaded end of the screw 180 is engaged with a threaded opening coaxial with this passage. As such, and as is known in the art, rotation of the thumb screw will cause the sides of the groove to be drawn together to thus reduce the diameter of the shaft opening 178. In this manner, the shaft 20 of the camera may be rigidly, yet releasably, secured.

The shaft lock 176 is mounted for horizontal rotation between the arms 174 of the support 172. This rotational axis is located such that it will pass through the longitudinal axis of the camera shaft 20. Preferably, the lock 176 is mounted upon nylon bearings within the arms 174, or some other arrangement which permits sterilization, as described more fully below. It is additionally noted that the vertical rotational axis of the gimbal pivot 40 with respect to the second pivot arm 38 also passes through the longitudinal axis of the camera shaft when the shaft is secured within the lock 176. While both axes pass through the shaft, the angular orientation of the support 172 places the horizontal axis outward of this vertical axis with respect to the second pivot arm. As may be envisioned from FIG. 1, this allows the camera shaft to be pivoted to a near-vertical position (or beyond) without the camera shaft abutting against the gimbal pivot.

With this arrangement, it may be readily seen that the camera shaft may freely rotate about a vertical and horizontal axis, both passing through its longitudinal axis, with respect to the second pivot arm 38.

While the gimbal 42 may be rigidly secured to the gimbal pivot 40, it is preferred that these two elements have a quick release mechanism. Such a quick release mechanism allows the camera to be readily disconnected from the majority of the system 10 in case of emergency. A preferred quick disconnect mechanism is shown in FIG. 11.

This quick disconnect mechanism is provided by forming the gimbal pivot 40 with a circular cavity 182 having an upward facing opening 184. The opening is also circular for the majority of its periphery, but has at least one projection 183 extending inward. Mounted within the cavity 182 for sliding movement is a gimbal lock 186. This sliding movement is between first and second positions, with the gimbal lock 186 being located outside the periphery of the opening 184 in the first position, and extending into or within the periphery of the opening 184 in the second position. A spring (not shown) is located between the gimbal lock and the gimbal pivot 40 to bias the gimbal lock to the second position. Finally, there is additionally provided a lock button 188 secured to the gimbal lock 186 and extending outwardly from the gimbal pivot 40.

The lower end of the support 172 of the camera gimbal 42 is provided with a circular flange 190. The flange 190 may be closely received through the opening 184 by tilting of the flange to pass by projection 183. The flange has a thickness such that it may be received within the cavity 182 with the gimbal locks 186 extending over the flange to closely retain the flange within the cavity. To provide a more secure fit, the periphery of the flange may be tapered, with the bottom faces of the projection 183 and locks 186 having a mating taper.

As may be envisioned, the lock button 188 may be manually pressed inward against the biasing force of the spring to move the gimbal locks 186 into the first position beyond the periphery of the opening 184. In this position the flange 190 of the gimbal may be inserted into the opening. Removal of the manual pressure will allow the gimbal lock 186 to move from the first position to the second position, over the flange 190. This will prevent removal of the flange 190 from the gimbal pivot 40 until the lock button 188 has been manually depressed once again. This arrangement allows the camera gimbal 42 to be securely retained upon the gimbal pivot 40, yet quickly released if need arises.

Additionally, this arrangement is very compatible with an easy method of reducing contamination (both of the system 10, and of the medical environment in which it may be used). In particular, the camera gimbal 42 may be removed from the gimbal pivot 40 and a sterile plastic sleeve slid over the pivot arms, and then over the slide arm. This will eliminate the need to sterilize the entire system 10, with only the gimbal requiring sterilization. The plastic sleeve, moreover, will not interfere with the mounting of the gimbal 42 in the pivot 40, nor will this mounting tear the plastic sleeve.

The above description completes the physical structure of the preferred embodiment of the system 10. As may be envisioned, this physical embodiment is readily suited to carry out the camera movement desired for the present application. In particular, should the user look to the right or to the left, the first and second pivot arms may be moved such that the gimbal 42 will circumscribe a horizontal arc about the trocar 16. Since the camera is capable of free rotation about a vertical axis on the second pivot arm (due to the pivotal mounting of the gimbal pivot 40), the camera is free to be rotated about the trocar 16, with the elasticity of the abdominal wall permitting the movement in the trocar 16. This will result in a movement of the camera which produces a pan to the left or right in the image displayed by monitor 25.

In a similar manner, when the user looks up or down, the lift arm 34 may be raised or lowered, and the pivot arms appropriately moved, such that the gimbal circumscribes a vertical arc about the trocar 16. As the camera shaft is rotatable about the horizontal axis due to the camera gimbal 42, the camera shaft is free to pivot about the trocar 16. This will result in an up or down elevation change in the image displayed by the monitor.

Finally, should the user move her or his head inward or outward, the pivot arms and lift arm may be moved to cause the camera shaft to slide in and out along a radial line extending from the trocar while maintaining the axis of the camera shaft in a stable position. This will result in a zoom or pullback in the image displayed by the monitor.

From the above description it is apparent that, in the present application, there are three basic camera movements. The first is a horizontal right or left pan of the camera. This movement will be known as azimuth change. The second movement is a rotation about a horizontal axis through the trocar, resulting in a vertical up and down movement of the view provided by the camera. This movement will be referenced as elevation. The third movement is inward and outward along a radial line extending from the trocar, which is referenced as zoom. To achieve each of these three basic movements, the control means must provide control signals to provide the desired movement of the lift arm to the proper vertical location, the first pivot arm to a proper angular orientation with respect to the lift arm, and the second pivot arm to a proper angular orientation with respect to the first pivot arm.

With reference to FIGS. 12, 12a and 13, the mathematical relationship of the arms, camera shaft and trocar are shown as an aid to explaining how the necessary relative positions of the arms may be calculated for any given desired camera movement.

With reference to FIG. 12, there is shown a schematic top view of the first and second pivot arms 36 and 38, the camera shaft 20, and the trocar 16. To begin, the first pivot arm, when viewed from above, will rotate about an axis located upon the lift arm 34. As such, the first end of the first pivot arm 36, corresponding to the first drive shaft 138, is the origin for an X-Y coordinate system. The first pivot arm 36 extends outwardly from the origin, has a length of $L_1$, and forms an angle $\alpha$ with the X axis. This angle $\alpha$ is known to the control means from the position sensor associated with shaft 138.

The second pivot arm 38 is connected for rotation to the first pivot arm by shaft 140. The second pivot arm has a length $L_2$, and forms an angle $\beta$ with the first pivot arm. This angle $\beta$ is known to the control means from the position sensor associated with shaft 140. The second pivot arm 38 terminates in the gimbal pivot 40 at which point the camera shaft 20 is pivotally connected to the second pivot arm. Finally, the camera shaft 20 extends from the pivot 40 to the pivotal connection provided by the trocar 16. In this top view, the camera shaft 20 will provide a projected length P. As may be seen, this results in a system having four links (one possibly having a varying length) and four revolute joints.

FIG. 13 shows the same system in a vertical plane extending through the longitudinal axis of the camera shaft, with the Z axis extending upward. In this view the true length of the shaft 20 is shown, and is identified as length $L_c$.

As should be apparent, for the control means to calculate the necessary movements to achieve a desired position, the control means must first know the current position. As such, and as will be described more fully below, there is a required initial setup procedure for the system 10. In brief, this procedure includes manual actuation of the lift release handle 124 and the arm release handle 160, such that the motor means are disconnected from each of the arms. This allows the arms to be easily moved manually, and the arms are manually moved until the bottom face of the gimbal pivot 40 is just above the trocar 16 on the patient. This is shown in FIG. 12a.

The control means uses the positions of the arms at this calibration point to calculate the relative position of the trocar 16 which will receive the camera. In particular, the control means will employ known and sensed information to calculate a distance R from the pivot axis on the lift arm to the trocar, and an angle $\theta$ from the X axis. This may be achieved by first calculating the X and Y coordinates of the pivot 40, and thus the trocar 16 using the equations $$X_{40}=L_1 \cos(\alpha)+L_2 \cos(\alpha+\beta)$$

$$Y_{40}=L_1 \sin(\alpha)+L_2 \sin(\alpha+\beta)$$

Thereafter, the values for R and $\theta$ may be calculated as $$R=(X_{40}^2+Y_{40}^2)^{\frac{1}{2}}$$

$$\beta=\cos^{-1}(X_{40}/R)$$

These values for R and $\theta$ will be stored and used for later calculations to find actual and desired arm positions. Additionally, the control means will also store the vertical position of the lift arm at this calibration position as a value Z. The actual stored value of Z may be modified slightly to take into account the difference in height ($Y_v$) between the bottom of arm 38 below the pivot 40 and the horizontal pivot axis of the camera within the gimbal 42. It is noted that these values will be retained until a new calibration/initialization procedure is performed.

Once these values have been stored, the arms may be manually moved clear the trocar. The camera will be inserted into the trocar, and the gimbal (previously connected to the shaft) is attached to the pivot 40. This results in the configuration shown in FIG. 12, and now that the R, $\theta$ and Z values have been determined, attention will now return to FIGS. 12 and 13.

As noted above, the desired camera motions are azimuth, elevation, and zoom. As such, the angles and lengths associated with these motions are first identified. In particular, FIG. 12 shows an angle $\gamma$ between the (local) X axis and the shaft 20 of the camera, about the trocar 16. This angle will correspond to azimuth.

With reference to FIG. 13, the angle $\lambda$ will correspond to the elevation of the camera. Finally, the full actual length of the shaft between the pivot 40 and trocar 16, $L_c$, corresponds to the zoom.

The general operational flow of the control means, better described below with reference to the program flowchart, is to first determine the current azimuth, elevation and zoom values. This is done by calculation from the current sensed arm positions. Then, the user's head movements are sensed to determine the desired change in camera position, such as two degrees left in azimuth. The control means then adds the desired change to the current position to determine the desired position in terms of azimuth, elevation and zoom. Once this desired position is found, the control means then calculates the actual arm positions needed to achieve the desired position. Finally, the control means effects the movement of the arms from the current to the desired position.

Based upon this, the first task is to determine the current azimuth, elevation and zoom based upon the sensed current arm positions.

Initially, it is noted that the projected length P of the shaft 20 may be found as follows $$P_x=X_{16}-X_{40}$$

where $$X_{40}=L_1 \cos(\alpha)+L_2 \cos(\alpha=\beta)$$

and $$X_{16}=R \cos(\theta).$$

Similarly, $$P_y=Y_{16}-Y_{40},$$

with $Y_{16}$ and $Y_{40}$ being found in a similar manner. Thereafter, P is found as $$P=(P_x^2+P_y^2)^{\frac{1}{2}}.$$

This is the projected shaft length of from the vertical rotation axis of the gimbal pivot to the trocar 16. Where the support 172 is angled as in FIG. 1, a portion of this projected length is due to the support 172, and is designated as $Y_h$. The actual projected length of the shaft from the lock to the trocar, $P_a$, would thus be found by subtracting $Y_h$ from P.

Now that the projected shaft length $P_a$ is known, it is possible to use the arm and shafts to calculate the position of the trocar. There are therefore two available methods to calculate the X and Y position of the trocar 16. Setting these two methods equal yields $$X: R \cos(\theta)=L_1 \cos(\alpha)+L_2 \cos(\alpha+\beta)+P \cos(\gamma-180°)$$

$$Y: R \sin(\theta)=L_1 \sin(\alpha)+L_2 \sin(\alpha+\beta)+P \sin(\gamma-180°)$$

noting that $\cos(\theta-180°)=-\cos(\theta)$ and $\sin(\theta-180°)=-\sin(\theta)$, $\gamma$ may be found by the equation $$\gamma=\cos^{-1}((L_1 \cos(\alpha)+L_2 \cos(\alpha+\beta)-R \cos(\theta))/P).$$

Again, where the support 172 is angled, the denominator P in the above equation is more properly represented as $(P_a+Y_h)$. As $\gamma$ is now known, the current azimuth is known.

The remaining values to be found are the elevation and zoom. With reference to FIG. 13, it is noted that if the shaft 20 is viewed as a right triangle, the projected length P will form the adjacent side, with the actual length, $L_c$, forming the hypotenuse. The opposite side is equal to the vertical distance between the gimbal and the trocar. However, this distance is equal to the current sensed position of the lift arm, minus the value Z (the vertical position at the trocar). This distance will be referenced as H.

$$L_c = (P^2 + H^2)^{\frac{1}{2}}$$

and $$\lambda = \cos^{-1}(P/L_c).$$

Again, it is noted that the angled support 172 may alter this calculation. If the support is angled, the $P_a$ value should be substituted for P, and the vertical offset of the support, $Y_v$, should be added to H.

At this point the current azimuth, elevation and zoom are known for the camera. The desired change to these values may then be added or subtracted to determine the desired azimuth, elevation and zoom, with these values being indicated as $\gamma'$, $\lambda'$ and $Z'$, respectively. From these desired values, it is necessary to calculate the desired arm positions.

The arm positions for a desired azimuth will be considered first. To begin, it is noted that P and $\lambda$ remain constant, and $\gamma'$ is known. As such, $$X_{40}' = R\cos(\theta) + P\cos(\gamma')$$

$$Y_{40}' = R\sin(\theta) + P\sin(\gamma')$$

and $$K = (X_{40}'^2 + Y_{40}'^2)^{\frac{1}{2}} \quad (1)$$

$$\Phi = \cos^{-1}(X_{40}'/K). \quad (2)$$

From this it may be shown that $$\Psi = \cos^{-1}((L_1^2 - L_2^2 - K^2)/-2KL_1) \quad (3)$$

$$\delta = \cos^{-1}((L_1^2 - L_2^2 + K^2)/2KL_1). \quad (4)$$

Subdividing the triangle $L_1$, $L_2$, K with a line perpendicular to K yields $$\omega' = 90° - \delta \quad (5)$$

$$\omega'' = 90° - \Phi. \quad (6)$$

The actual arm positions desired are therefore $$\alpha' = \Phi + \delta \quad (7)$$

$$\beta' = 180° - \omega' - \omega''. \quad (8)$$

A change in elevation is now considered. It is first noted that $\gamma$ and $L_c$ will remain constant, and the new value $\lambda'$ is known. With reference to FIG. 13, H' may be quickly found as $$H' = L_c \sin(\gamma').$$

Additionally, $$P_a' = L_c \cos(\gamma').$$

If the support 172 is angled, the vertical constant $Y_v$ should thereafter be added to H', and the the horizontal constant $Y_h$ should thereafter be added to $P_a'$ to determine P'. Since $\theta$, R, $\gamma$ and P' are now known, equations (1)-(8) above may be used to determine the values for $\alpha'$ and $\beta'$.

Finally, a change in zoom will be considered. With a change in zoom, $\gamma$ and $\lambda$ will remain constant, and the new value $L_c'$ will be known. Again, it may be quickly found that $$H' = L_c' \sin(\gamma)$$

$$P' = L_c' \cos(\gamma),$$

although again these values should be modified for the angled support 172, if necessary. As before, equations (1)-(8) above may now be used to calculate the values for $\alpha'$ and $\beta'$.

Having thus described how the control means 28 may determine its present position and calculate the joint position for the desired position, the general program flow for the control means 28 will now be described.

With reference to FIG. 14 there is shown a main loop program for the control means 28. As a first step upon powering up, the program will initialize variables, perform self-diagnostics, set up communications ports, and various other common tasks. Next, the program will initialize the sensing unit 46 and verify that it is tracking the module 48 upon the headset 50 of the user.

The program will then find the head position, and as may be seen this is the first step in the true loop of the program. It is noted that, depending upon the sensing unit and module employed, it may be necessary to reformat the output of the sensing unit 46 to a local representation of the head position.

After the head position has been found from the input signal from the sensing unit, the program will check the status of a mode selection switch 192 (FIG. 1). The mode selection switch has two positions, one for normal operation and one for the initialization of the system (where the position of the trocar is found). This initialized condition will be discussed first.

When the mode switch 192 is in the initialization position, the user will release the motors from the arms and manually move the arms until the gimbal pivot 40 is just above the trocar 16, as discussed above. At that point the foot control switch 58 is activated once to move the control switch from the stop to the run position. While a continued presence in either the stop or the run condition will have little effect, the transition between these two conditions will trigger the control means to store the output from the position sensors connected to the arms.

The control means may then calculate the position of the trocar (and in particular the values R, $\theta$ and Z) such that the later motions may be calculated. From this point the motors are disabled to ensure that the there is no motion of the arms. The program will then continue through normal flow until the mode selection switch is moved into the normal position. As the remainder of the normal program flow will be discussed below, it is not discussed at this point.

When the selection switch 192 has been moved to the normal position, the control means will check the status of the foot control switch 58. This switch may have two conditions, run and stop. As noted above, when the foot switch is in the run condition the user's head motions will be translated into camera motions. When in the stop position the user may freely move his or her head without causing camera movement. Finally, the transition from the stop to the run condition causes the control means to save the head position as a null position.

This general flow is shown in FIG. 14, where there are three possibilities upon checking the status of the foot switch. If there is a transition from the stop to the run position, the program will save that head position as the null position and will then will use the information from the arm position sensors to calculate the current azimuth, elevation and zoom ($\gamma$, $\lambda$ and $L_c$). As the system will now be in the run condition, the servos are also enabled.

Where the foot switch is found to be currently in the stop condition the program simply branches to the disable motor command discussed above, and where the system is found to be currently in the run condition, the program branches to the next step after enabling the motors.

In particular, after the motors have been enabled, the program will subtract the null position (found at the moment of stop to run condition transition) from the head position found during the first step of the main loop. As noted above, this head position input signal may include varying amounts of data, up to the three dimensional position and orientation of the module, fixing its exact position within space. For the present embodiment, all predetermined head movements may be found using only the orientation about a vertical axis (azimuth), orientation about a lateral axis (elevation), and position along a front to rear axis (zoom).

The next task performed by the program may be to investigate the head motion and perform a correction for the pitching action of the head. In particular, the human head will pivot about the neck at a point approximately even with the bottom of the jaw. As the module is located at the top of the headset, if a user nods his or her head, the module will move horizontally, vertically, as well as rotating. The horizontal component of a pure nod could therefore be taken erroneously as a zoom command. This step is therefore a first correction of the head motion to reduce the value detected for horizontal movement of the module if there is rotation associated with a nod, and may take a general form of (predetermined value corresponding to average distance from "jaw" pivot to module)*sin(angle of rotation of module caused by nodding). A similar correction may be performed to reduce the front/rear motion inherent in moving the head from right to left.

After this initial correction of the head position information, the head position information is saved within a table. It is preferred that several of the most recent positions be saved, and in the preferred embodiment eight positions are employed. The "actual" position information (modified by the previous step) may be directly saved, or prior to saving the position information may be modified further such that it is "smoothed" to a more average value in line with previous values saved in the table. It is of course apparent that the values in this table must be deleted with each storing of a new null position.

Using the latest head position information from the table, along with some or all of the previous head position information in the table, the various velocities of the head movement may be calculated. As noted above, in this particular application the velocities of interest will be a turning of the head to the left and the right (azimuth), a nodding of the head up and down (elevation), and a movement of the head forward and backward (zoom).

As the next step in program flow, the program calculates or calls up a "window" variable for each of the possible head movements. Head positions within this window will not result in any camera movement, and the head position must exceed, or go out of, this window to produce camera movement. As such, this defines a null zone to eliminate camera movement based upon unintentional head movement. In addition to defining this basic window, the window size may be varied according to the setting upon a sensitivity knob 194 (FIG. 1).

At this point the head position and head velocities have been determined. Therefore, using the head position and velocity information, a value is assigned to a variable LEDb. This variable indicates if there will be a required change in azimuth, elevation, or a zoom, and whether this change is positive or negative. Note that this variable includes information (preferably an on/off condition of a bit) which is analogous to an on/off switch for each motion, with no amplitude information. Upon completing this task, the appropriate light upon indicator 60 is activated to inform the user that the control system 28 is in the head tracking mode.

It should be noted that the illumination of the light on the indicator 60 at this particular time has no dependence upon any of the calculated values. As such, the green light on indicator 60 will be illuminated regardless of the velocities of the head, position of the head within the window, or other variables. In practice, the entire main program loop will cycle at least at a rate of approximately 40 to 60 times per second. Therefore the user will perceive the LED as being illuminated the entire time the system is in the run condition. It is noted that this is the case in the preferred embodiment, however, other possibilities are available.

As the next step in program flow, the various motions of the head are considered. In particular, the position of the head is checked to determine if it is beyond the window (calculated above), such that camera motion may be activated. Additionally, however, the velocity of the head is also considered. Specifically, the head velocity in the particular direction must be above some predefined threshold limit for camera motion to be enabled. If the head position is within the window, or if the head velocity is below the threshold, the corresponding portion of the variable LEDb is set to "0" (or some other value), thus cancelling the camera position command for that particular motion (either azimuth, elevation, or zoom).

The next step is to compare the current camera position with the variable LEDb. If the variable LEDb is attempting to command a camera motion which is beyond a predefined limit of motion for the camera (such as the camera moving too far out of the trocar 16, or the camera shaft being fully inserted within the trocar) that particular motion command within the variable LEDb will be set to "0" or other appropriate variable to cancel that motion command.

The program next moves to the step of determining an amplitude for each motion enabled by the variable LEDb, based upon what are referred to as deltas. In particular, for each particular motion (elevation, azimuth, or zoom), the motion of the camera is preferably quite smooth during use. To assure this, a table of various predetermined values is provided for each of the three motions. Within these tables are delta values which vary from a negative maximum value to some positive maximum value. It is preferred that the increments between values in this table are rather small.

A pointer is associated with each of the delta tables, with the pointer identifying which particular value within the delta table will be used. The pointers are incremented or decremented upon each iteration of the main loop depending upon the motion commands specified in the variable LEDb. For example, the first time the variable LEDb contains a motion command for a change in elevation, the pointer for the elevation delta table will be identifying the zero value. Upon the next iteration of the main loop, if the variable LEDb still contains a motion command for a similar change in elevation, the pointer will be moved to a non-zero, although small, value.

With each iteration of the main loop, where a change in elevation is continued to be specified, the pointer will move to a larger and larger value within the table, until the maximum value is reached. Further iteration with an elevation change will maintain the pointer at this maximum value. In a similar manner, where an elevation change has been specified previously in the LEDb, but is no longer specified, the pointer will be decremented such that the values in the delta table will be reduced with each iteration. It is preferred that the delta values drop off at a greater rate than they are increased.

This delta value will be used as a base number for the amplitude of motion change. As may be envisioned, this will reduce abrupt starts and stops in camera motion, smoothing the camera motion in accordance with the varying delta values.

The program will next scale the delta values found in the previous step according to a position of a speed knob 196 (FIG. 1). This is typically a straight multiplying factor based upon the knob setting. With this speed knob 196 the user may thus determine the speed of the camera motion.

The delta values are again scaled by the next step of program operation. In particular, the delta values are scaled according to the current zoom position of the camera. This current zoom position may be a value roughly corresponding to the relative zoom ($L_c$) of the camera, and stored with each iteration. It is noted that this value should be maintained even after a new null position is defined by use of the foot control switch 58. As may be envisioned, where the camera is zoomed into a detailed view of a structure, small changes in elevation or azimuth will result in very large changes in the view shown by monitor 25. As such, the delta values will be reduced with increasing zoom to allow for finer motions in magnified views.

Upon completing this step, the program will perform one more scaling function upon the delta values. This scaling initially compares the three possible motions reported by the sensing unit as input. As it is difficult for humans to obtain a pure azimuth, elevation, or zoom motion, an attempt by the user to move his or her head to the left or right to effect an azimuth input will typically result in a large azimuth reading, along with additional smaller motions corresponding to one or both of the remaining directions. As such, the three motion variables in the input are compared, and one or two of the three possible motions will be attenuated if it (or they) are a sufficient amount smaller than the largest of the three motions. This particular step can make the system 10 much easier for beginners to operate.

As beginners may have much more trouble with the proper head motions compared with experienced users, the amount of attenuation performed in this step may be controlled by an attenuation knob 198. This will allow the user to vary the attenuation as their skill increases.

At this point the delta values initially found have been scaled for various factors, and the desired camera motion has thus finally been defined. The program as its next step will use these deltas to calculate the desired changes in camera position to thus find the desired positions ($\gamma'$, $\lambda'$, and $L_c'$). Using the equations described above, the program can then determine the desired arm joint angles and slide arm vertical position ($\alpha'$, $\beta'$, and H'). Once the desired joint angles have been calculated, the program will determine the present arm positions by reading the position sensors from the various joints and slides.

As the final step in the main loop, the PID controller uses at least the current arm joint positions, desired arm joint positions, previous errors and arm velocities to calculate motor speed command variables. There will of course be one motor speed command variable for each of the motors driving the slide arm 34, first pivot arm 36 and second pivot arm 38.

Upon completing this calculation of the motor speed commands, the program returns to the beginning of the loop and finds the next head position. It may be desirable to initialize the sensing unit each pass, or upon a predetermined number of passes, before finding the next head position, as a method of avoiding errors based upon input problems. As noted previously, it is preferred that the main program loop operate at least at approximately 40 to 60 hertz. This is believed to be a sufficiently high rate that the camera motion will track the head movements with great accuracy. Additionally, it is noted that with this high number of iterations per second, the desired change in position of the various arms will be small for any given iteration. As such, this eliminates the possibility of the motion of the pivot arms between two widely spaced positions will be effected by moving the gimbal to move in a straight line between these two widely spaced positions. As has been noted previously, for the elevation and azimuth movements, the gimbal must move in a circular pattern about the trocar 16 to maintain a constant zoom position. By providing a large number of very small movements, this is achieved.

Figure 15:
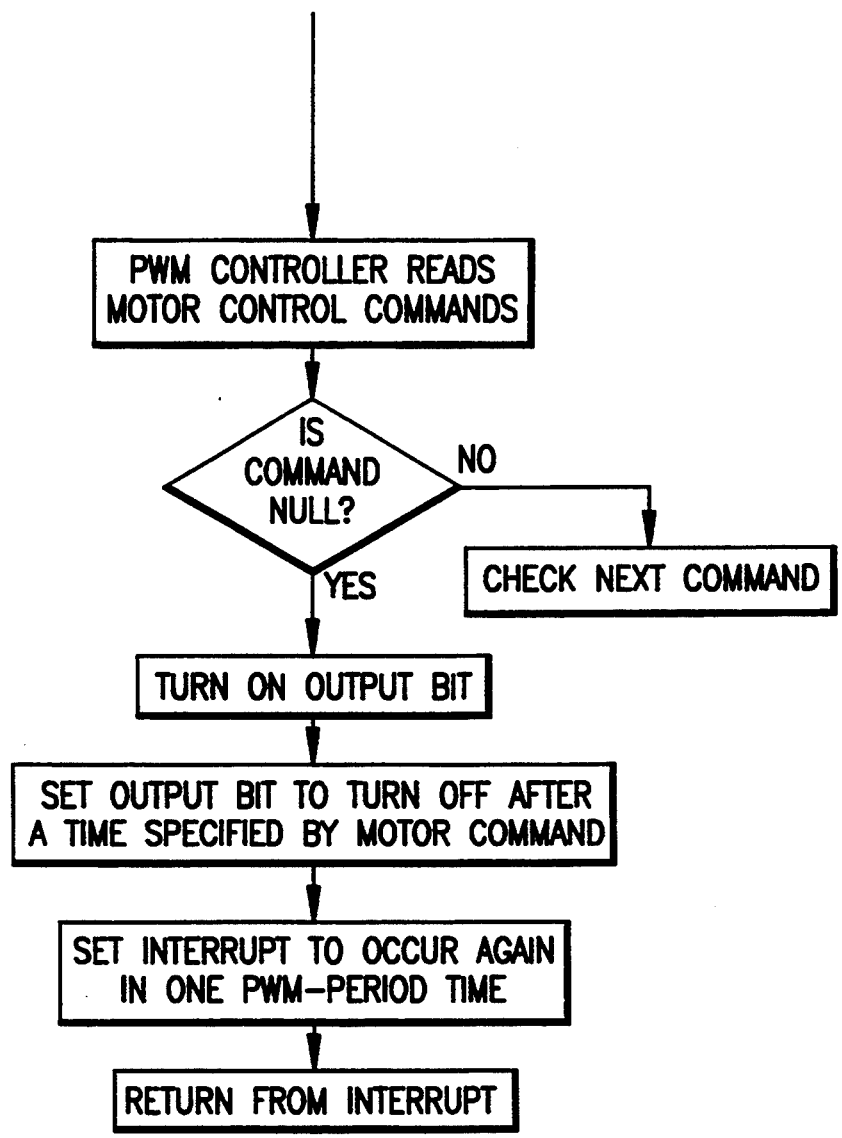

With reference to FIG. 15, there is shown an interrupt routine of the program of FIG. 14, which employs the motor speed commands to cause actual motor activation. In particular, upon encountering an interrupt (described more fully below), the PWM controller reads the motor speed commands generated by the main loop. The interrupt routine then checks to make sure that the command is not a null command for each motor, and if an actual command is received for at least one motor, it moves onward. With a command received, the interrupt routine sets an output bit corresponding to the desired motor to "1". As the next step, the interrupt routine sets this output bit to "0", but only after a time specified by, or based upon, the associated motor speed command. The interrupt routine then sets an interrupt to occur again after one PWM period time has elapsed. The interrupt routine thereafter returns to the main program flow. As may be envisioned, after this one PWM period time as elapsed as set in the interrupt routine, an interrupt will be called again, transferring control to the interrupt routine.

Upon consideration of the above, it may be seen that the system 10 according to the present invention provides remote control of a robotic apparatus based on sensed movements of the human body. In the present application, the robotic apparatus is connected to a camera, with the output of the camera being viewed and directed by the user. As such, the portion of the human body which is sensed to control the robotic apparatus has been chosen as the head. With appropriate equipment it is also possible to sense the orientation of the user's eyes and direct the robotic apparatus based upon this information.

While the invention has been described with regard to a medical camera, other applications employing other robotic apparatus may be controlled according to the present method. One closely related example would be camera types other than for laparoscopic surgery, such as surveillance or manufacturing cameras. As another example, a bull dozer could be remotely controller using the headset and module of the present invention. The left and right head movements for azimuth could cause a left or right turn of the bull dozer, the nodding azimuth movements of the user's head could be used to raise and lower the blade of the bull dozer, and the forward and back zoom motions of the user's head could be used to adjust speed of the bull dozer. Other head movements could be used for other functions. Control of various other apparatus using the headset and module of the present invention may readily be envisioned.

It is also noted that, even where a similar application for telescopic medicine is desired, a robotic apparatus different than that specifically described may be employed. For example, the present apparatus employs a linear lift arm 34 to raise and lower the pivot arms. As an alternative, the lift arm may be rigid and have a horizontal pivot axis with the first pivot arm to cause raising and lowering. As such, the apparatus would resemble a human shoulder and arm. Other variations are of course possible. For example, the arms may eliminate all pivotal movement, and simply provide linear movement of the arms with respect to each other, in a manner similar to a plotter.

Even within the lift arm/dual pivot arm apparatus disclosed, various modifications may of course be made. For example, the various motor means may take different form. Different motors other than those specifically shown may be employed, different gear arrangements, and different gear release arrangements may be used. As a specific example, rather than moving the travel gear perpendicular to its rotation axis, the travel gear may be moved along its axis of rotation into and out of engagement with the other gears. As such, these arrangements may be generally designated as means for selectively engaging and disengaging the motor means.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. A control system for a remote apparatus, said apparatus being capable of movement in at least one direction based upon a predefined motion of the human body, said predefined motion having a positive and a negative direction with respect to a null position of the human body, said control system comprising:

at least one module constructed and arranged to be mounted upon a portion of the human body which will undergo the predefined motion;

a sensing unit for determining at least one attribute of said module selected from the group consisting of: a position of said module with respect to a second portion of the human body; a position of said module with respect to the ground, an orientation of said module with respect to a second portion of the human body, and an orientation of said module with respect to the ground; at least one of said module and said sensing unit providing input signals relating to said attribute;

a control switch movable between first and second conditions;

control means receiving said input signals and generating output signals to cause said movement of said apparatus, said control means being operatively connected to said control switch to monitor said condition of said switch, said control means (1) in said first condition of said switch, not causing said movement of said apparatus, (2) upon said switch moving from said first to said second condition said control means taking said attribute from said input signal as the null position of the human body, and (3) in said second position of said switch said control means evaluating said input signal to determine a rate of change of said attribute, to determine whether said attribute changes is consistent with the predefined motion of the human body, and to determine whether the predefined motion is in the positive or the negative direction, said control means causing said movement of said apparatus when said rate of change of said attribute is above a predetermined limit, and said attribute change does correspond to the predefined motion, and the predefined motion is in the positive direction.

2. A control system as in claim 1, wherein said control means, with said control switch in the second position, will not cause said movement of said apparatus when the predefined motion is determined to be in the negative direction.

3. A control system as in claim 2, wherein said module is constructed and arranged to be mounted upon the head of the human body.

4. A control system as in claim 3, wherein said control means, upon said control switch moving from said first to said second position, additionally determines a null window from said null position in the positive direction, and said control means, when said control switch is in said second position, (1) determines whether said attribute corresponds to said module moving beyond said window, and (2) said control means not causing said movement of said apparatus when said module has not moved beyond said window.

5. A control system as in claim 4, wherein said control means includes a manual sensitivity adjustment, said control means determining the size of said null window as a function of a position of said sensitivity adjustment.

6. A control system as in claim 4, wherein said wherein said control means may cause a plurality of distinct movements of said apparatus, each said movement being associated with a discrete predefined motion of the human body.

7. A control system as in claim 6, wherein said predefined motions include nodding the human head up and down, swiveling the human head left and right, and causing forward and backward translation of the human head.

8. A control system as in claim 7, wherein said control system, when said control switch is in said second position, determines the relative sizes of said attribute changes corresponding to said predefined motions, and attenuate any resulting movement of said apparatus corresponding to at least a smallest of said attribute changes.

9. A control system as in claim 8, wherein said control means includes a manual attenuation adjustment, said control means attenuating said resulting movement as a function of said attenuation adjustment.

10. A control system as in claim 7, in combination with said apparatus, and wherein said apparatus includes a medical telescopic video camera, and wherein said movements of said apparatus result in at least elevation, azimuth or pan, and zoom of a video image produced by said camera, said movements being respectively associated with the nodding, swiveling, and translating motions of the human head.

11. The combination of claim 10, wherein said control means, when said control switch is in said second position, determines the relative zoom of said camera, and attenuate said movements when said camera has a high zoom factor.

12. The combination of claim 10, wherein said apparatus includes a mount for said camera, said mount including:
 a mount portion constructed and arranged to be secured to a medical table;
 a slide arm connected to said mount portion and capable of substantially vertical motion with respect to said mount portion;
 a first pivot arm having first and second ends, a first end of said pivot arm being connected to said slide arm and capable of oscillation with respect to said slide arm about a substantially vertical axis;
 a second pivot arm having first and second ends, a first end of said second pivot arm being connected to said second end of said first pivot arm and capable of oscillation with respect to said first pivot arm about a substantially vertical axis;
 a gimbal assembly connected to said second end of said second pivot arm, said gimbal assembly mounting said camera, and being capable of rotation with respect to said second pivot arm about a substantially vertical axis and about substantially horizontal axes;
 means for moving said lift arm with respect to said mounting portion, operatively connected to said control means;
 means for moving said first pivot arm with respect to said lift arm, operatively connected to said control means; and
 means for moving said second pivot arm with respect to said first pivot arm, operatively connected to said control means.

13. The combination of claim 12, wherein said gimbal assembly includes a gimbal pivot connected to said second end of said second pivot arm for rotation about a substantially vertical axis, a support secured to said gimbal pivot for rotation therewith, and a lock portion connected to said support for rotation about a substantially horizontal axis, said lock portion mounting said camera.

14. The combination of claim 13, wherein said support is manually releasably connected to said gimbal pivot.

15. A robotic mount for a medical telescopic camera, comprising:
 a mount portion constructed and arranged to be secured to a medical table;
 a slide arm connected to said mount portion and capable of substantially vertical motion with respect to said mount portion;
 a first pivot arm having first and second ends, a first end of said pivot arm being connected to said slide arm and capable of oscillation with respect to said slide arm about a substantially vertical axis;
 a second pivot arm having first and second ends, a first end of said second pivot arm being connected to said second end of said first pivot arm and capable of oscillation with respect to said first pivot arm about a substantially vertical axis;
 a gimbal assembly connected to said second end of said second pivot arm, said gimbal assembly mounting said camera, and being capable of rotation with respect to said second pivot arm about a substantially vertical axis and about substantially horizontal axes;
 means for moving said lift arm with respect to said mounting portion;
 means for moving said first pivot arm with respect to said lift arm; and
 means for moving said second pivot arm with respect to said first pivot arm.

16. The combination of claim 15, wherein said gimbal assembly includes a gimbal pivot connected to said second end of said second pivot arm for rotation about a substantially vertical axis, a support secured to said gimbal pivot for rotation therewith, and a lock portion connected to said support for rotation about a substantially horizontal axis, said lock portion mounting said camera.

17. The combination of claim 16, wherein said support is manually releasably connected to said gimbal pivot.

* * * * *